United States Patent [19]
Treiber

[11] Patent Number: 5,264,593
[45] Date of Patent: Nov. 23, 1993

[54] CHOLESTEROL LOWERING COMPOUNDS

[75] Inventor: Laszlo R. Treiber, Gillette, N.J.

[73] Assignee: Merck & Co., Inc., Rahway, N.J.

[21] Appl. No.: 6,007

[22] Filed: Jan. 15, 1993

[51] Int. Cl.$^5$ .............................. A61K 31/335
[52] U.S. Cl. ............................................ 549/363
[58] Field of Search ................................ 549/363

[56] References Cited

U.S. PATENT DOCUMENTS

| | | | |
|---|---|---|---|
| 5,096,923 | 3/1992 | Bergstrom et al. | 514/452 |
| 5,102,907 | 4/1992 | Bergstrom et al. | 514/456 |
| 5,132,320 | 7/1992 | Bergstrom et al. | 514/452 |

FOREIGN PATENT DOCUMENTS

WO92/22660  6/1992  PCT Int'l Appl. ............ 549/363

OTHER PUBLICATIONS

U.S. Ser. No. 07/715,518, Jun. 1991, Trieber et al.
U.S. Ser. No. 07/938,981, Sep. 1992, Berger et al.
U.S. Ser. No. 07/979,559, Nov. 1920, Trieber et al.

*Primary Examiner*—James H. Reamer
*Attorney, Agent, or Firm*—Charles M. Caruso; Melvin Winokur; Catherine A. Dolan

[57] ABSTRACT

This invention relates to compounds of structural formula

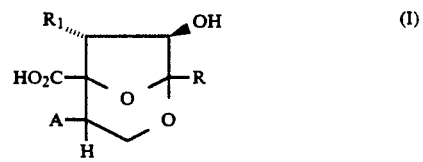

which are inhibitors of squalene synthase and useful as cholesterol lowering agents.

4 Claims, No Drawings

CHOLESTEROL LOWERING COMPOUNDS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e., several grams at a time and they are not very palatable.

MEVACOR ® (lovastatin) and ZOCOR ® (simavastatin), now commercially available, are members of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to unbiquinone, dolichol and isopentenyl t-RNA.

Previous efforts at inhibiting squalene synthetase have employed pyrophosphate or pyrophosphate analogs containing compounds such as those described in P. Ortiz de Montellano et al, *J. Med Chem.* 20, 243 (1977) and E. J. Corey and R. Volante, *J. Am. Chem. Soc.*, 98, 1291 (1976). S. Biller (U. S. Pat. No. 4, 871, 721) describes isoprenoid (phosphinylmethyl) phosphonates as inhibitors of squalene synthetase.

Recently certain nonphosphorous containing inhibitors of squalene synthetase have been isolated as natural products. These natural product inhibitors are described in U.S. Pat. Nos. 5,096,963 and 5,132,320 and 5,102,907. Semisynthetic analogs of these naturally ocurring compounds have been reported in EPO 512,865 publication. A need still remains for a more effective squalene synthetase inhibitors, i.e., one that provides a greater antihypercholesterolemic effect and exhibits a good safety profile.

The natural product inhibitors are tricarboxylic acids. The present applicants have now found that these natural products known as zaragozic acid A, zaragozic acid B and zaragozic acid C can be transformed following a photochemical conversion to the compounds of the present invention, which are potent cholesterol lowering agents.

DETAILED DESCRIPTION OF THE INVENTION

This invention relates to compounds of structural formula (I):

1. A compound of formula (I)

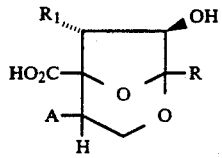

(I)

wherein
R is selected from

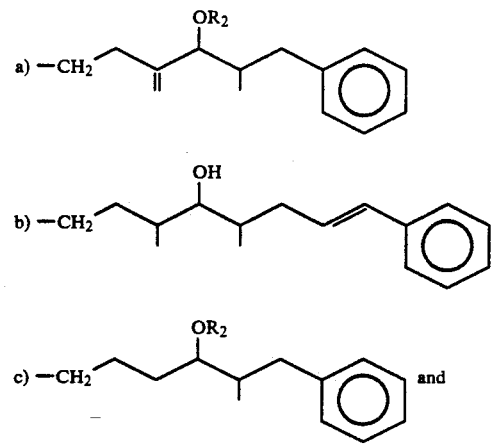

$R_1$ is selected from

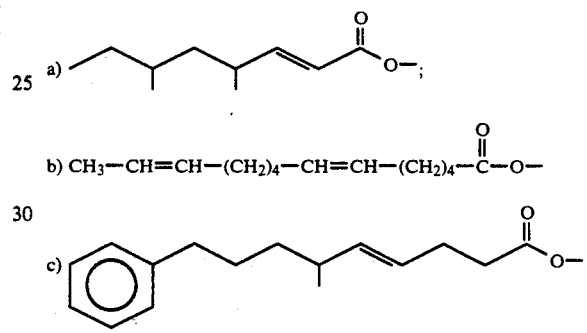

and $R_2$ is selected from

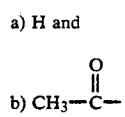

provided that when R is

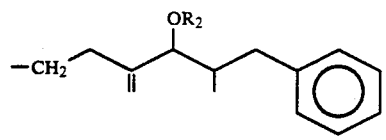

then $R_1$ is

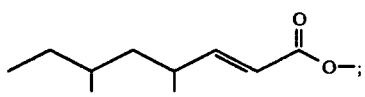

and when R is

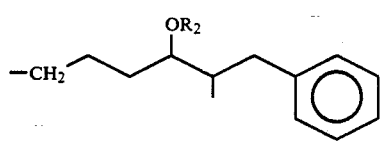

then $R_1$ is

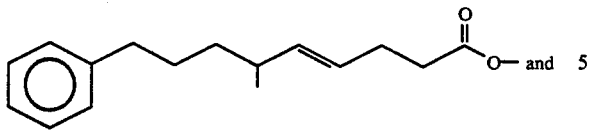

When R is

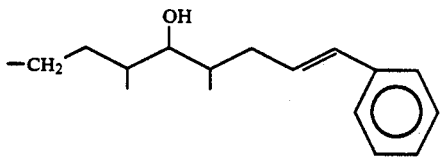

then $R_1$ is

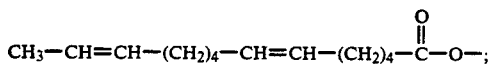

A is selected from
a) $NR_3R_4$;
b) $C_{1-5}alkylCO_2-$;
c) $CO_2H-C_{1-3}\ alkyl-CO_2-$;
d) $NR_3R_4R_5$;
wherein $R_3$, $R_4$ and $R_5$ are each independently selected from:
a) hydrogen;
b) $C_{1-5}alkyl$;
c) Aryl $C_{1-5}alkyl$;
wherein Aryl is phenyl or naphthyl.

This invention is illustrated by those compound wherein
R is

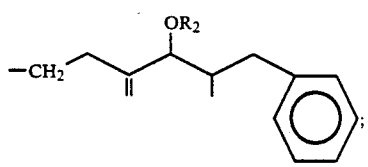

$R_1$ is

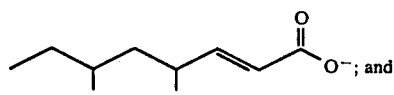

$R_2$ is H or

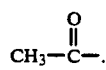

Exemplifying this illustration are those compounds wherein $R_2$ is $CH_3C(O)$ and A is
(a) $NH_2$;
(b) $CH_3CO_2-$;
(c) $CH_3CH_2CO_2-$;
(d) $CH_3CH_2CH_2CO_2-$;
(e) $CH_3C(CH_3)_2CO_2-$;
(f) $CO_2CH_2CH_2CO_2-$.

Compounds of formula (I) are squalene synthase inhibitors and are useful as cholesterol lowering agents and anti-fungal agents. Compounds of formula (I) are prepared from compounds of formula (II):

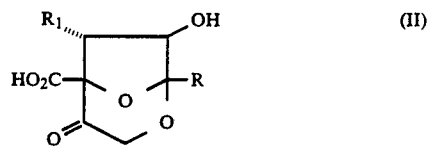

Compounds of formula (I) wherein A is amino or substituted amino are prepared by treating a compound of formula (II) with ammonia or a substituted amine in the presence of reducing conditions such as hydrogen over Raney nickel. Alternatively the amino group may be inserted by treatment of the oxime of the appropriate ketone with $NaBH_4$ in the presence of titanium trichloride. Formation of the amine salt can be accomplished by treatment with mineral acid and the formation of a quaternary ammonium salt by treatment of the ternary amine with an alkyl or arylalkyl iodide. Compounds of formula (I) wherein A is alkanoyl or carboxy alkanoyl are prepared by reducing a compound of formula (II) to its corresponding alcohol with sodium borohydride. The alcohol is subsequently treated with the appropriate acylating agent such as the acid anhydride. Compounds of formula (II) can be formed from zaragozic acid A (U.S. Pat. No. 5,096,923), zaragozic acid B (U.S. Pat. No. 5,132,320) and zaragozic acid C (U.S. Pat. No. 5,102,907) by photochemical treatment of the parent natural products, under exposure to air, and preferably in the presence of an appropriate catalyst such as $Fe^{3+}$, in a polar aprotic solvent such as DMSO, $CH_3CN$ or DMF. Compounds of formula (II) wherein $R_2$ is acetate can be converted to compounds wherein $R_2$ is H by a biotransformation. A culture of MF6817 (ATCC 55189 has been employed in this transformation.

The present invention is also concerned with a method of treating hypercholesterolemia which comprises the adminsitration to a subject in need of such treatment a nontoxic therapeutically effective amount of a Compound I, or a pharmaceutically acceptable salt thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but a daily dosage for adults is within a range of from about 20 mg to 2000 mg (preferably 20 to 100 mg) which may be given in two to four divided doses. Higher doses may be favorably employed as required.

The present invention is also concerned with a method of inhibiting squalene synthetase which comprises the administration to a subject in need of such treatment a nontoxic therapeutically effective amount of a Compound I, or a pharmaceutically acceptable salt thereof. Specifically, the compounds of this invention are useful in treating disease conditions such as, but not limited to, hypercholesterolemia conditions which require the action of the enzyme squalene synthase. They may be administered by the same routes in the same dosages as described for the method of treating hypercholesterolemia.

The pharmaceutically acceptable salts of the compounds of this invention include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylaimine, piperazine, tris(hydroxymethyl)aminomethane, and tetramethylammonium hydroxide.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-CoA synthase inhibitors, and squalene epoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemgibrozil. Appropriate daily dosages for adults are niacin (0.5 to 8 gm), probucol (up to 1000 mg), clofibrate (up to 2 gm) and gemfibrozil (800–1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methy-(3-trimethylaminopropyl) iminotrimethylene dihalide]. The relative amounts of the compounds of this invention and these polymers is between 1:100 and 1:15,000.

The intrinsic squalene synthetase inhibitory activity of the compounds of this invention was measured by the standard in vitro protocol described below:

PREPARATION OF HUMAN HepG2 cell ENZYME

1. SOURCE: HEPG2 CELL LINE (Liver, hepatoblastoma, Human) ATCC No. HB 8065
2. CELL GROWTH AND MAINTENANCE Culture Medium: Minimum essential medium (MEM) with non-essential amino acids, sodium pyruvate, and 10% fetal bovine serum. The medium was changed twice weekly. A confluent monolayer was achieved in 1 week. The growth medium is prepared as listed below.

| | Solution | Volume (ml) |
|---|---|---|
| 1. | MEM (Gibco #320-1090AK) With Earle's salts and L-glutamine | 1000 |
| 2. | Penicillin (10,000 units/ml), streptomycin (10,000 mg/ml), Gibco #600-5140 PG | 10 |
| 3. | MEM sodium pyruvate, 10 mM (100X) Gibco #320-1140 | 10 |
| 4. | MEM nonessential amino acids, 10 mM(100X) Gibco #320-1140AG | 10 |
| 5. | L-glutamine, 200 mM (100X), Gibco #320-5030AG | 10 |
| 6. | Hyclone fetal bovine serum, defined, Hyclone #A-111-L | 100 |

Subculture Procedure: Remove medium, wash with PBS, add fresh trypsin (0.25%)-EDTA (0.02%) with Hank's Balanced Salt solution and let flask stand for a minute and remove the trypsin solution. Incubate flask at 37° C. until cells detached. Add fresh medium, disperse and dispense cells into new flasks. Subcultivation ratio: 1:6.

PREPARATION of Delipidated Serum: Fetal calf serum (100 ml) and CAB-O-Sil (2 grams) stir overnight at 4° C. and centrifuge at 16,000 rpm for 5 hrs. Filter supernatant and store at 4° C.

48 hrs. prior to harvest, switch cells grown in MEM with 10% Fetal Calf serum to MEM with 10% delipidated serum.

3. Harvest: Remove medium, wash with PBS, add fresh trypsin (0.25%)-EDTA (0.02%) with Hank's Balanced Salt solution, rinse and remove. Incubate flask at 37° C. until cells detach. Add 6 ml of MEM medium per flask to suspend cells and combine into centrifuge tube. Spin cells at 1,000 rpm for 5 mins. Wash by resuspending cell pellet in PBS and repeat centrifuging. Count cells ($2.5 \times 10^9$ yield from 18 flasks (75 cm$^2$). Resuspend in 10 mls of 50 mM HEPES (N-[2-Hydroxyethyl]piperazine-N'-[2-ethane-sulfonic acid]) containing 5 mM $MgCl_2$, 2 mM $MnCl_2$, 10 mM DTT, pH 7.5 (enzyme suspension buffer).

4. Cell Extracts: Sonicate (probe sonicator setting #60, pulse) the cell suspension on ice for 2 min. After a 1 min. cooling on ice, the sonication is repeated until greater than 90% of the cells are broken as observed microscopically. Centrifuge cell suspension for 10 mins. at 10,000 rpm. Transfer supernatant to clean tube and centrifuge at 20,000 rpm for 20 mins. The HepG2 enzyme preparation was centrifuged at 34,000 rpm to separate the cytosol and microsomal enzymes. The enzyme suspension was diluted 1 to 250 and used to perform the squalene synthetase assay using 3 μM $^3$H-farnesyl pyrophosphate as the substrate.

Squalene Synthase Assay

Reactions were performed in 1.2 ml polypropylene tube strips of 8. Buffer mixture and substrate mixture for the assay were prepared from the following solution:

Buffer mixture contains 270 mM HEPES, pH 7.5, 20 mM Potassium fluoride and 5.4 mM Dithiothreitol(DTT). 55 μl of this mixture was used per assay. The final concentrations of HEPES, KF and DTT in the assay are 150 mM, 11 mM and 3 mM respectively.

| Substrate mixture: | | | |
|---|---|---|---|
| | Stock concentration | μl used per assay | Final concentration |
| 1. | $MgCl_2$, 20 mM | 10 | 6 mM |
| 2. | NADPH, 3 mM (made fresh) | 10 | 1 mM |
| 3. | Squalene Epoxidase inhibitor, Banyu FW-439H, 0.5 mg per ml | 0.02 | 1 μg per ml |
| 4. | $^3$H-farnesyl-pyrophosphate, 25 mM, 20 Ci per mole | 2.4 | 0.6 μM |
| 5. | Farnesyl-pyrophosphate, 3 mM | 0.08 | 2.4 μM |
| 6. | Water | 7.5 | |

For each reaction, 55 μl of buffer mixture was taken with 5 μl of an inhibitor solution in DMSO and 10 μl of diluted enzyme (1 to 250 as described in the enzyme preparation, the final protein concentration of enzyme in the assay is 2 μg per ml.). The inhibitor solution was prepared by dissolving dry sample in DMSO. The reaction was initiated by the addition of 30 μl of substrate solution and the mixture was incubated at 30° C. for 20 minutes. The reactions were stopped by the addition of 100 μl of 95% EtOH, vortexed, and 100 μl of a suspension of 1 gram per ml of Bio-Rad AG 1×8 resin (400 mesh, Chloride form) was then added, vortexed. 300 μl of heptane was added to each tube strip and the strips were capped and vortexed for 10 minutes. 150 μl of heptane layer was then removed into a 96 deep well plate and mixed with 150 μl of scintillation fluid and the radioactivity was determined by liquid scintillation counting. The controls were run with 5 μl of DMSO and blanks were run with the addition of 100 μl of 95% EtOH to denature the enzyme before the addition of the substrate mixture to the assay tube.

Percent inhibition is calculated by the formula:

$$\frac{(Control - Sample) \times 100}{Control - Blank}$$

$IC_{50}$ values were determined by plotting the log of the concentration of the test compound versus the percentage inhibition. The $IC_{50}$ is the concentration of inhibitor that give 50% inhibition as determined from these plots. The $IC_{50}$ for representative compounds of this invention are:

| | |
|---|---|
| Example 1 | 1.9 ng/ml |
| Example 2 | 40 ng/ml |

EXAMPLE 1

4-Acetate of 3,4-decarboxy-4-epi-Zaragozic Acid A 3,4-decarboxy-4-epi-Zaragozic Acid A (140 μg) was dissolved in acetic anhydride (0.2 ml). The solution was kept at room temp. for 1.5 hrs. Acetic anhydride was evaporated in nitrogen stream at 40° C. The dry residue containing the titled product was redissolved in methanol (0.2 ml) for HPLC assay and prep. HPLC purification.

The analytical HPLC was carried out on a Beckman Ultrasphere Octyl column (250×4.6 mm) in gradient elution mode. Solvent A: 10 mM $H_3PO_4$ in water; Solvent B: acetonitrile-water (85:15 v/v). The gradient program was as follows: from 0-2 min 80% B, from 2-14 min. linear gradient from 80% to 100% B and from 14-24.5 min. 100% B. The flow rate was constant at 0.90 mL/min. The retention times of the starting alcohol and product ester were 9.3 min. and 11.3 min., resp.

The preparative HPLC purification of the product was performed on a Beckman Ultrasphere Octyl column (250×10 mm) in gradient elution mode. Solvent A: 0.1% HCOOH in water; Solvent B: 0.1% HCOOH in acetonitrile-water (85:15 v/v). The gradient program was as follows: from 0-15 min. 80% B, from 15-16.5 min. linear gradient from 80% to 100% B and from 16.5 min. to 30 min. 100% B. The flow rate was constant at 4.00 mL/min. The retention times of the starting alcohol and product ester were 11.2 min. and 15.6 min., resp.

EXAMPLE 2

4-Trimethylacetate of 3,4-decarboxy-4-epi-Zaragozic Acid A 3,4-decarboxy-4-epi-Zaragozic Acid A (120 μg) was dissolved in trimethylacetic anhydride (0.10 mL). The solution was kept at room temp. for one hour. Methanol (ca. 0.5 mL) was added to the solution. The mixture was evaporated in nitrogen stream at 40° C. The dry residue containing the titled product was redissolved in methanol (0.2 mL) for analytical HPLC and prep. HPLC purification.

The HPLC procedures were the same as described under Example 1. The retention times of the product ester in anal. HPLC and prep. HPLC were 14.8 min. and 20.5 min., resp.

EXAMPLE 3

4-Propionate of 3,4-decarboxy-4-epi-Zaragozic Acid A 3,4-decarboxy-4-epi-Zaragozic Acid A (148 μg) was dissolved in propionic anhydride (0.20 mL). The solution was kept at room temp. for one hour. The mixture was evaporated in nitrogen stream at 40° C. A few drops each of water, methanol and acetic acid were added to the dry residue. The sample was then dried again in a nitrogen stream. The residue containing the titled product was redissolved in methanol (0.2 mL) for analytical and prep. HPLC.

The HPLC procedures were the same as described under Example 1. The retention times of the product ester were 12.6 min. and 18.6 min. in analytical and prep. HPLC, resp.

EXAMPLE 4

4-Butyrate of 3,4-decarboxy-4-epi-Zaragozic Acid A 3,4-decarboxy-4-epi-Zaragozic Acid A (148 μg) was dissolved in butyric anhydride (0.10 mL). The solution is kept at room temp. for 2 hours. The reaction mixture was then evaporated to dryness in a nitrogen stream at 40° C. A few drops each of water, methanol and acetic acid were added to the dry residue. The sample was then dried again in nitrogen stream. The residue containing the title product was redissolved in methanol (0.2 mL) for analytical and prep. HPLC.

The HPLC procedures were the same as described under Example 1. The retention times of the product ester were 13.9 min. and 19.9 min. in analytical and prep. HPLC, resp.

EXAMPLE 5

4-Succinate of 3,4-decarboxy-4-epi-Zaragozic Acid A 3,4-decarboxy-4-epi-Zaragozic Acid A (160 μg) was dissolved in a mixture of acetonitrile (0.50 ml) and pyridine (10 μL). Succinic anhydride (0.11 g) was added. The reaction mixture was kept at room temp. for 5.5 hours. The sample was evaporated to dryness in nitrogen stream at 40° C. A few drops each of water, ethanol and acetic acid were added to the dry residue. The sample was evaporated again. The dry residue containing the product ester was redissolved in methanol (0.25 mL) for analytical and prep. HPLC.

The analytical HPLC was carried out on a Beckman Ultrasphere Octyl column (250×4.6 mm) in gradient elution mode. Solvent A: 10 mM $H_3PO_4$ in water; Solvent B: acetonitrile-water (85:15 v/v). The gradient program was as follows: from 0-2 min 40% B, from 2-18 min. linear gradient from 40% to 100% B and from 18-24.5 min. 100% B. The flow rate was constant at 0.90 mL/min. The retention times of the starting alcohol and product ester were 19.3 min. and 19.0 min., resp.

The preparative HPLC purification of the product is performed on Beckman Ultrasphere Octyl column (250×10 mm) in gradient elution mode. Solvent A: 0.1% HCOOH in water; Solvent B: 0.1% HCOOH in acetonitrile-water (85:15 v/v). The gradient program is as follows: from 0–19 min. 70% B, from 19–20.5 min. linear gradient from 70% to 100% B and from 20.5 min. to 30 min. 100% B. The flow rate was constant at 4.00 mL/min. The retention times of the starting alcohol and product ester were 21.8 min. and 22.0 min., resp.

EXAMPLE 6

4-Dehydroxy-4-amino-3,4-decarboxy-4-epi-Zaragozic Acid A

Tartaric acid (450 mg, 3 mmol) is dissolved in water (20 ml). The pH of the solution is adjusted to 7.0 with NaOH. Aqueous solution of titanium trichloride (0.9M, 0.35 mL) is added to a tartarate solution. The pH is adjusted again to 7.0. Water is added to the solution to a volume of 50 ml before using it in the reaction below.

Working in nitrogen atmosphere NaBH$_4$ (0.102 mg, 2.7 $\mu$mol) is added to 0.5 mL of the above titanium trichloride solution in tartarate buffer immediately before adding the oxime of 4-keto-4-dehydroxy-3,4-decarboxy Zaragozic Acid A (583 $\mu$g, 0.95 $\mu$mol) dissolved in 2-propanol (1.0 ml) to the mixture. The sample is stirred for 24 hrs. At the end of the reaction the sample is extracted with ethylacetate. The organic phase is evaporated to dryness in nitrogen stream at 40° C. The dry residue containing the titled product is redissolved in methanol (0.25 mL) for analytical and prep. HPLC.

EXAMPLE 7

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

EXAMPLE 8

Preparation of an Ammonium Salt

A 0.1 mmol sample of the free acid of a compound of formula (I) is dissolved in 10 ml of methanol. The resulting solution is mixed with a stoichiometric amount of aqueous ammonia after which the ammonium salt precipitates from solution.

EXAMPLE 9

Preparation of a Potassium Salt

A solution of 0.1 mmol of the free acid of a compound of formula (I) in 10 ml of methanol is treated with an aqueous or methanolic solution containing 0.1 mmol of potassium hydroxide. Evaporation of the solvent affords the potassium salt. In a similar fashion the sodium and lithium salts can be formed.

EXAMPLE 10

Preparation of a Calcium Salt

A solution of 0.1 mmol of the free acid of a compound of formula (I) in 20 ml of 6:4 methanol/water is treated with an aqueous solution of 0.05 mmol of calcium hydroxide. The solvents are evaporated to give the corresponding calcium salt.

EXAMPLE 11

Preparation of an Ethylenediamine Salt

A solution of 0.1 mmol of the free acid of a compound of formula (I) in 10 ml of methanol is treated with 0.05 mmol of ethylenediamine. Evaporation of the solvent affords the ethylenediamine salt.

The procedure can also be applied to the preparation of the N,N''-dibenzylethylenediamine salt.

EXAMPLE 12

Preparation of a Tris(hydroxymethyl)aminomethane Salt

To a solution of 0.1 mmol of the free acid of a compound of formula (I) in 10 ml of methanol is added about 0.1 mmol tris(hydroxymethyl)aminomethane dissolved in 10 ml of methanol. Evaporation of the solvent gives the titled salt. Similarly prepared are the salts of L-ornithine, L-lysine, and N-methylglucamine.

EXAMPLE 13

Preparation of an L-arginine Salt

A solution of 0.1 mmol of the free acid of the compound of formula (I) in 10 ml of 6:4 methanol/water is treated with an aqueous solution of 0.1 mmol of L-arginine. Evaporation of the solvent affords the title salt.

Similarly prepared are the salts of L-ornithine, L-lysine and N-methylglucamine.

What is claimed is:

1. A compound of formula (I)

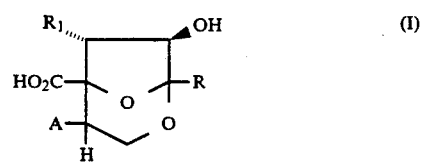

wherein
R is selected from a) 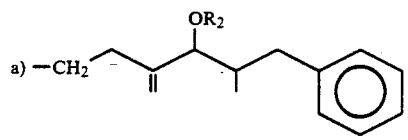

b) 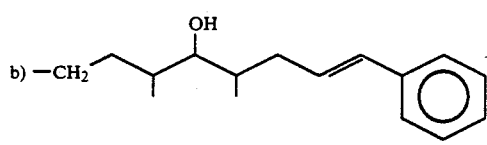

c) 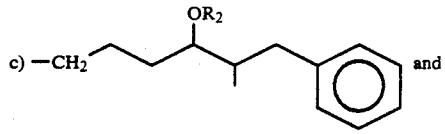 and $R_1$ is selected from a) 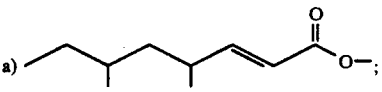

b) 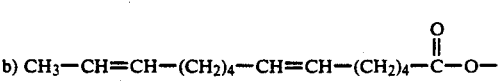

c) 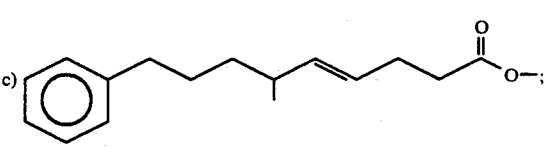

-continued and

R₂ is selected from a) H and $$b)\ CH_3-\overset{\overset{O}{\|}}{C}-$$

provided that when R is

[structure: -CH₂-CH=C(OR₂)-CH(CH₃)-CH₂-phenyl]

then R₁ is

[structure: CH₃CH₂-CH(CH₃)-CH(CH₃)-CH=CH-C(=O)-O-]

and when R is

[structure: -CH₂-CH₂-CH(OR₂)-CH(CH₃)-CH₂-phenyl]

then R₁ is

[structure: phenyl-CH₂CH₂CH₂-CH(CH₃)-CH=CH-CH₂-C(=O)-O- and]

when R is

[structure: -CH₂-CH(CH₃)-CH(OH)-CH(CH₃)-CH₂-CH=CH-phenyl]

then R₁ is $$CH_3-CH=CH-(CH_2)_4-CH=CH-(CH_2)_4-\overset{\overset{O}{\|}}{C}-O-;$$

A is selected from
    a) NR₃R₄;
    b) C₁₋₅alkylCO₂—;
    c) CO₂H—C₁₋₃ alkyl—CO₂—;
    d) —NR₃R₄R₅;
    wherein R₃, R₄ and R₅ are each independently selected from
    a) hydrogen;
    b) C₁₋₅alkyl; and
    c) ArylC₁₋₅alkyl;
    d) wherein Aryl is phenyl or naphthyl;
or a pharmaceutically acceptable salt thereof.

2. A compound of claim 1 wherein
R is

[structure: -CH₂-CH=C(OR₂)-CH(CH₃)-CH₂-phenyl];

R₁ is

[structure: CH₃CH₂-CH(CH₃)-CH(CH₃)-CH=CH-C(=O)-O-; and]

R₂ is H or $$CH_3-\overset{\overset{O}{\|}}{C}-.$$

3. A compound of claim 2 wherein R₂ is CH₃C(O)—.
4. A compound of claim 3 wherein
A is selected from
    (a) NH₂;
    (b) CH₃CO₂—;
    (c) CH₃CH₂CO₂—;
    (d) CH₃CH₂CH₂—CO₂—;
    (e) CH₃C(CH₃)₂—CO₂—
    (f) CO₂—CH₂CH₂—CO₂—

\* \* \* \* \*